(12) United States Patent
Amoros et al.

(10) Patent No.: US 7,939,691 B2
(45) Date of Patent: May 10, 2011

(54) PREPARATION OF PRIMARY DIAMINES

(75) Inventors: Daniel Amoros, Venissieux (FR); Denis Rachez, St Genis Laval (FR)

(73) Assignee: Rhodia Operations, Aubervilliers Cedex (FR)

( * ) Notice: Subject to any disclaimer, the term of this patent is extended or adjusted under 35 U.S.C. 154(b) by 0 days.

(21) Appl. No.: 12/308,688

(22) PCT Filed: Jun. 15, 2007

(86) PCT No.: PCT/FR2007/000998
§ 371 (c)(1),
(2), (4) Date: Sep. 3, 2009

(87) PCT Pub. No.: WO2007/147960
PCT Pub. Date: Dec. 27, 2007

(65) Prior Publication Data
US 2010/0036169 A1    Feb. 11, 2010

(30) Foreign Application Priority Data
Jun. 20, 2006   (FR) ...................................... 06 05464

(51) Int. Cl.
*C07C 209/48*    (2006.01)
(52) U.S. Cl. .......................... 564/492; 564/491; 564/498

(58) Field of Classification Search .................... None
See application file for complete search history.

(56) References Cited

U.S. PATENT DOCUMENTS

| | | | |
|---|---|---|---|
| 3,017,331 A | | 1/1962 | Campbell et al. |
| 6,139,693 A * | | 10/2000 | Bassler et al. .................. 203/49 |
| 6,887,352 B2 * | | 5/2005 | Ostermaier ........................ 203/2 |
| 2006/0058545 A1 * | | 3/2006 | Ostermaier .................... 558/452 |
| 2006/0058555 A1 * | | 3/2006 | Ostermaier .................... 564/511 |

FOREIGN PATENT DOCUMENTS
GB        731 819        6/1955

OTHER PUBLICATIONS

International Search Report corresponding to PCT/FR 2007/000998 issued on Jan. 3, 2008.

* cited by examiner

*Primary Examiner* — Brian J Davis
(74) *Attorney, Agent, or Firm* — Buchanan Ingersoll & Rooney, P.C.

(57) ABSTRACT

Primary diamines are prepared by hydrogenation of a dinitrile compound in the presence of a catalyst, in particular hexamethylenediamine is prepared by hydrogenation of adiponitrile; the product diamines are recovered by distillation in several distillation columns mounted in series and the heavy impurities are separated from the second distillation.

6 Claims, 1 Drawing Sheet

PREPARATION OF PRIMARY DIAMINES

CROSS-REFERENCE TO PRIORITY/PCT APPLICATIONS

This application claims priority under 35 U.S.C. §119 of FR 0605464, filed Jun. 20, 2006, and is a continuation/national phase of PCT/FR 2007/000998, filed Jun. 15, 2007 and designating the United States (published in the French language on Dec. 27, 2007, as WO 2007/147960 A3; the title and abstract were also published in English), each hereby expressly incorporated by reference in its entirety and each assigned to the assignee hereof.

The present invention relates to a process for the manufacture of a primary diamine by hydrogenation of a dinitrile compound in the presence of a catalyst.

It relates more particularly to a process for the manufacture of hexamethylenediamine by hydrogenation of adiponitrile.

Hexamethylenediamine is a chemical intermediate of great importance, used in particular as monomer in the manufacture of polyamides. Thus, hexamethylenediamine is used in combination with adipic acid to form an amine salt, hexamethylenediamine adipate, also known as Nylon salt. This salt is employed in the manufacture of poly(hexamethylene adipamide), more usually known as PA 6,6.

Hexamethylenediamine is also an important chemical intermediate in the manufacture of diisocyanate compounds.

The processes for the manufacture of hexamethylenediamine used industrially consists in hydrogenating a dinitrile compound, namely adiponitrile, in the presence of a catalyst.

Thus, several hydrogenation processes are known and made use of. They can be classified into two main groups according to the catalyst used and the temperature and pressure conditions.

In the first group of processes, the catalyst is generally a metal oxide, such as iron oxide or cobalt oxide.

The hydrogenation is carried out at high pressures and temperatures and often in the presence of ammonia.

The second group comprises processes using metal catalysts of Raney type, such as Raney nickel or Raney cobalt. The hydrogenation can be carried out at a fairly low pressure and temperature. The Raney metal catalyst is often used in combination with doping metal oxides or metal elements. In order to maintain the activity and the selectivity of this type of catalyst, it is necessary and obligatory to use a strong base.

In these two groups of processes, the hydrogenated products and in particular hexamethylenediamine are recovered in the pure form by a sequence of distillations intended to remove water and the light impurities, on the one hand, and the heavy impurities, on the other hand.

The term "light impurities" is understood to mean, in the field of the distillation of organic compounds, the compounds exhibiting a lower boiling point than that or those of the hydrogenated compounds which have to be recovered.

Likewise, the impurities referred to as "heavy impurities" are those which exhibit a higher boiling point than that of the hydrogenated compounds.

The formation of heavy or light impurities will be more or less favoured or more or less limited according to the conditions under which the hydrogenation process is carried out.

However, impurities are necessarily formed as they are generated by the decomposition of certain compounds or by reaction between the molecules present.

Mention may be made, among these impurities, of hexamethyleneimine (HMI), diaminocyclohexane (DCH), tetrahydroazepine (THA) or aminomethylcyclopentenamine (AMCPA).

The majority of these impurities are a hindrance in the use of hexamethylenediamine, in particular as monomer in the manufacture of polyamides. This is because they can generate impurities in the polyamide obtained, causing a yellow colouring of the latter and inhomogeneities in the material which bring about defects and breakages, in particular during the manufacture of yarns.

The presence of these impurities or compounds is detected and measured in particular by polarographic analysis, expressed quantitatively by the polarographic index (PI) or moles of THA per million moles of HMD, and by gas chromatography analysis, for the determination of the HMI, DCH and AMCPA concentrations.

It is therefore necessary to employ a process for the recovery of the hydrogenated compounds, such as hexamethylenediamine, present in the hydrogenation reaction medium which makes it possible to obtain these compounds with a high degree of purity.

Figure 1:
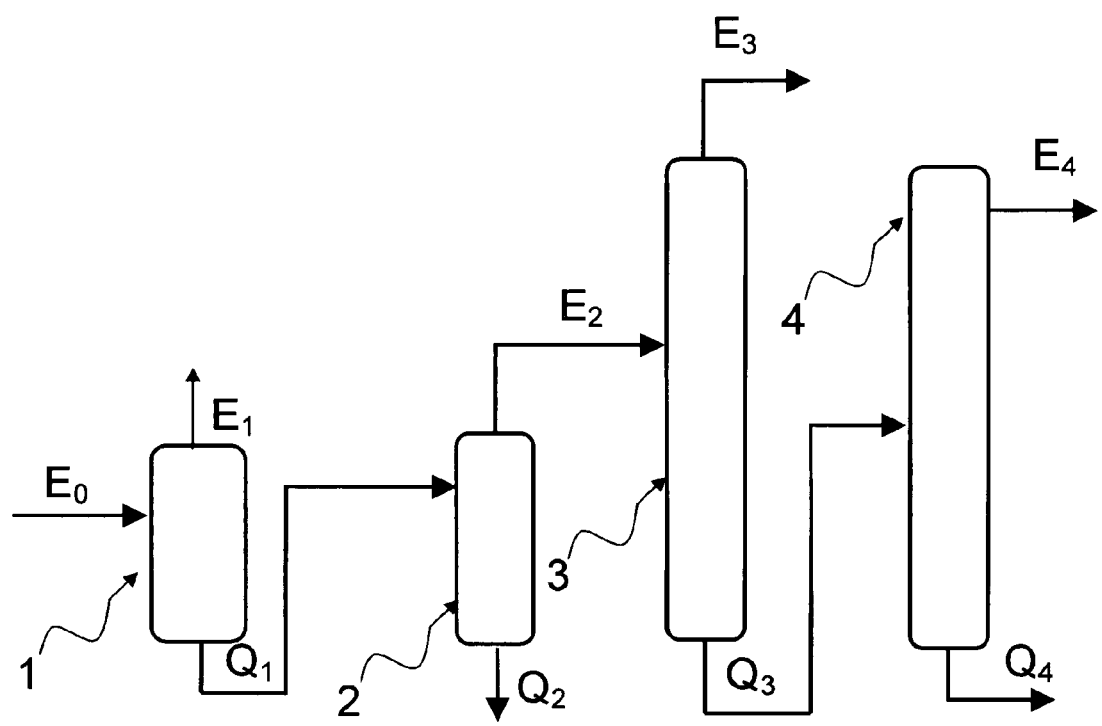
FIG. 1 is a schematic representation of a process for manufacturing diamines by hydrogenation of dinitriles.

A process for the recovery of hexamethylenediamine comprising a first distillation of the hydrogenation reaction medium in order to remove the water has already been provided. The impurity hexamethyleneimine (HMI) is also removed in this distillation column as it is entrained by the distilling water.

The bottom fraction collected in this first distillation is subjected to a second distillation in which the light impurities are removed.

The pure hydrogenated product, such as hexamethylenediamine, is obtained in a third distillation of the bottom fraction recovered in the second distillation.

The heavy impurities are removed in the bottom fraction from this third distillation stage.

There are a number of disadvantages to this sequence of distillations. In particular, it can be difficult to obtain a hexamethylenediamine exhibiting a high purity. Furthermore, the energy consumption is high.

One of the aims of the present invention is to provide a process for the manufacture of diamines by hydrogenation of dinitriles comprising a process for the recovery of the diamine which makes it possible to obtain, in a controlled way, a pure diamine with minimized energy consumption.

To this end, the invention provides a process for the manufacture of primary diamine compounds, more particularly of hexamethylenediamine (HMD), by hydrogenation of a dinitrile compound in the presence of a hydrogenation catalyst which consists in, successively:

Hydrogenating the dinitrile compound using hydrogen or a hydrogen-comprising gas and in recovering or withdrawing from this stage a stream $E_0$ comprising the hydrogenated compounds.

Subjecting the stream $E_0$ to a first distillation in order to recover a top fraction $E_1$ comprising water and the imines present (HMI) and a bottom fraction $Q_1$ comprising the hydrogenated compounds.

Subjecting the bottom stream $Q_1$ to a second distillation in order to recover, as bottom fraction $Q_2$, the compounds forming impurities with a boiling point greater than that of the hydrogenated compounds, known as "heavy" impurities, and, as top fraction $E_2$, a fraction comprising the hydrogenated compounds. These heavy impurities are generally referred to as "tars" in the field of organic chemistry.

Subjecting the top stream $E_2$ to a third distillation in order to recover a top fraction $E_3$ comprising the light compounds or impurities and a bottom fraction $Q_3$ comprising the hydrogenated compounds. and Subjecting the stream $Q_3$ to a fourth distillation in order to recover a top fraction $E_4$ composed of the pure diamines or hydrogenated compounds and a bottom fraction $Q_4$ comprising the heavy impurities.

This sequence of successive distillations makes it possible, from the second distillation, to remove the greater part of the compounds or impurities with a high boiling point or heavy impurities.

Thus, the removal at the beginning of the process of these "heavy" impurities makes it possible to improve and to facilitate the operation of the following distillations. By way of example, the fouling of the packing components of the columns is greatly reduced. In addition, the energy necessary to purify the diamine in the following distillations is minimized.

It is also advantageous, in order to limit the losses of diamines (hexamethylenediamine), to treat the fractions $Q_2$ and $Q_4$ comprising the "heavy" impurities. This treatment can be carried out in a conventional distillation column with distillation of the diamine or in columns of thin film evaporation type. The diamine recovered can advantageously be recycled in one of the preceding columns, such as the final distillation column or the column which makes it possible to separate the heavy impurities and to recover the fraction $Q_2$.

This process applies in particular when the hydrogenation stage is carried out in the presence of a catalyst based on a Raney metal, such as a Raney nickel or Raney cobalt, in combination with a strong inorganic base, such as sodium hydroxide or potassium hydroxide.

This is because the presence of a strong base can result in the formation of products of high molecular weight, in particular when the medium is heated to relatively high temperatures, such a those reached in the reboilers of the distillation columns.

The process of the invention applies in particular to the manufacture of hexamethylenediamine (HMD) by hydrogenation of adiponitrile in the presence of a catalyst based on Raney nickel.

The hydrogenation reaction is carried out in conventional devices for the implementation of this reaction and at standard temperature conditions.

Mention may be made, as example of the illustration of the implementation of this hydrogenation reaction, of the patents: FR 913 997, FR 1 463 409, BE 700 877, U.S. Pat. Nos. 3,821,305, 3,056,837, WO 00/37424 and WO 00/03972.

The various distillation stages are carried out in conventional and standard distillation devices, such as perforated plate columns, valve tray columns, packed columns, structured packed columns or plate columns.

The operating conditions for these columns will be shown in the detailed description of an embodiment of the invention.

The invention makes it possible to recover a hexamethylenediamine exhibiting a high purity corresponding to the specifications required in particular for the manufacture of a polyamide.

Other advantages and details of the invention will become more clearly apparent in the light of the detailed description of an embodiment of the process of the invention, with reference to the single appended FIG. 1, which represents a block diagram of this embodiment of the process of the invention.

A reaction medium $E_0$ originating from a stage of hydrogenation of adiponitrile, not represented, in the presence of a catalyst based on Raney nickel and of potassium hydroxide is fed to a distillation column 1. This column 1 operates under a pressure of 50 to 220 mmHg (6.6 kPa to 29.3 kPa) with a number of theoretical plates of between 5 and 20.

This column is a structured packed column.

This column 1, known as the dehydration column, makes it possible to recover, as top fraction $E_1$, the water present in the reaction medium and also hexamethyleneimine. The bottom fraction $Q_1$ comprises less than 50 ppm of water.

This fraction $Q_1$ is fed to a second distillation column 2 operating under a pressure of 50 to 250 mmHg (6.6 kPa to 33.3 kPa) with a number of theoretical plates of between 1 and 5.

The bottom fraction $Q_2$ is composed of compounds with a higher boiling point than that of hexamethylenediamine. It represents from 1 to 10% by weight of the heavy compounds present in the reaction medium $E_0$.

The top fraction $E_2$ is fed to a third distillation column 3 operating under a pressure of 10 to 80 mmHg (1.3 kPa to 10.6 kPa) with a number of theoretical plates of between 30 and 80. This column 3 is advantageously a packed column.

The bottom fraction $Q_3$ recovered exhibits a concentration of diaminocyclohexane (DCH) of less than 10 ppm.

The top fraction $E_3$ is composed of light compounds with a lower boiling point than that of hexamethylenediamine.

The bottom fraction $Q_3$ is fed to a fourth and final distillation column 4 operating under a pressure of 10 to 50 mmHg (1.3 kPa to 6.6 kPa) and with a number of theoretical plates of between 30 and 70. This column 4 is a plate column.

The hexamethylenediamine is recovered at the column top in the form of a stream $E_4$ comprising less than 2 ppm of tetrahydroazepine and with a PI of less than 15. The bottom fraction $Q_4$ comprises heavy compounds.

Advantageously, the bottom fractions $Q_2$ and $Q_4$ can be subjected to a treatment in order to extract the hexamethylenediamine present, for example by distillation in a distillation column or in a column with evaporation in the form of thin films (not represented).

The process of the invention, by removing a portion of the heavy compounds before the removal of the light compounds and the distillation of hexamethylenediamine, makes it possible to carry out a separation in the third and fourth columns with a minimum of energy and an excellent yield.

The invention claimed is:

1. A process for the preparation of a primary diamine by hydrogenation of a dinitrile compound in the presence of a hydrogenation catalyst, comprising:

hydrogenating the dinitrile compound with hydrogen or a hydrogen-containing gas;

subjecting the stream $E_0$ resulting from the hydrogenation medium to a first distillation and recovering a top fraction $E_1$ which comprises water and the imines present and a bottom fraction $Q_1$ which comprises the hydrogenated compounds;

subjecting the stream $Q_1$ to a second distillation and recovering a top fraction $E_2$ which comprises the hydrogenated compounds and a bottom fraction $Q_2$ which comprises compounds having a higher boiling point than the primary diamine;

subjecting the top fraction $E_2$ to a third distillation and recovering a bottom fraction $Q_3$ which comprises the hydrogenated compounds and a top fraction $E_3$ which comprises the compounds having a lower boiling point than that of the diamine compound formed; and subjecting the bottom fraction $Q_3$ to a fourth distillation and recovering a top fraction $E_4$ which comprises the pure diamine, and a bottom fraction $Q_4$ which comprises compounds having a higher boiling point than the primary diamine.

2. The process as defined by claim 1, wherein the catalyst comprises Raney nickel or Raney cobalt.

3. The process as defined by claim 1, wherein the hydrogenation is carried out in the presence of a strong inorganic base selected from the group consisting of sodium hydroxide and potassium hydroxide.

4. The process as defined by claim 1, wherein the distillation stages are carried out in distillation columns selected from the group consisting of perforated plate columns, plate columns, packed columns, valve tray columns and structured packed columns.

5. The process as defined by claim 1, wherein the fractions comprising heavy impurities, $Q_2$ and $Q_4$, are treated in a distillation column to recover the diamine and such recovered diamine is recycled to the second or fourth distillation.

6. The process as defined by claim 1, wherein the diamine is hexamethylenediamine and the dinitrile compound is adiponitrile.

* * * * *